(12) United States Patent
Wright et al.

(10) Patent No.: US 11,278,412 B2
(45) Date of Patent: Mar. 22, 2022

(54) HYBRID FIXATION FEATURES FOR THREE-DIMENSIONAL POROUS STRUCTURES FOR BONE INGROWTH AND METHODS FOR PRODUCING

(71) Applicant: DePuy Ireland Unlimited Company, Ringaskiddy (IE)

(72) Inventors: Abraham P. Wright, Warsaw, IN (US); Nicholas A. Miltner, Warsaw, IN (US); Weidong Tong, Warsaw, IN (US); Tyler S. Boggs, Warsaw, IN (US); Bryan J. Smith, Warsaw, IN (US)

(73) Assignee: DePuy Ireland Unlimited Company

(*) Notice: Subject to any disclaimer, the term of this patent is extended or adjusted under 35 U.S.C. 154(b) by 112 days.

(21) Appl. No.: 16/370,599

(22) Filed: Mar. 29, 2019

(65) Prior Publication Data

US 2019/0298525 A1 Oct. 3, 2019

Related U.S. Application Data

(60) Provisional application No. 62/650,790, filed on Mar. 30, 2018.

(51) Int. Cl.
*A61F 2/30* (2006.01)
*A61F 2/38* (2006.01)
*A61F 2/28* (2006.01)

(52) U.S. Cl.
CPC ...... *A61F 2/30771* (2013.01); *A61F 2/30767* (2013.01); *A61F 2/30907* (2013.01);
(Continued)

(58) Field of Classification Search
CPC .... A61F 2/30771; A61F 2/38; A61F 2/30907; A61F 2/30767; A61F 2/389;
(Continued)

(56) References Cited

U.S. PATENT DOCUMENTS 4,038,703 A * 8/1977 Bokros ............... A61F 2/06
623/2.38
4,479,271 A * 10/1984 Bolesky ............ A61F 2/30907
623/20.17

(Continued)

FOREIGN PATENT DOCUMENTS

EP 1800700 A2 6/2007
EP 2319462 A1 5/2011
(Continued)

OTHER PUBLICATIONS

Bobyn et al, Characteristics of bone ingrowth and interface mechanics of a new porous tantalum biomaterial; The Journal of Bone & Joint Surgery, vol. 81-B, No. 5, Sep. 1999, 907-914.
(Continued)

*Primary Examiner* — Jerrah Edwards
*Assistant Examiner* — Melissa A Hoban
(74) *Attorney, Agent, or Firm* — BakerHostetler

(57) ABSTRACT

An orthopaedic prosthetic component comprises a fixation peg including a porous three-dimensional structure configured to permit bone in-growth. The porous three-dimensional structure has an outer surface boundary. The fixation peg includes a plate attached to the porous three-dimensional structure at the outer surface boundary. The plate includes a tapered body having an outer wall that faces away from the porous three-dimensional structure and is devoid of any openings.

15 Claims, 9 Drawing Sheets

(52) U.S. Cl.
CPC ............... *A61F 2/38* (2013.01); *A61F 2/389* (2013.01); *A61F 2002/2892* (2013.01); *A61F 2002/30011* (2013.01); *A61F 2002/3092* (2013.01); *A61F 2002/3093* (2013.01); *A61F 2002/30594* (2013.01); *A61F 2002/30784* (2013.01); *A61F 2002/30827* (2013.01); *A61F 2002/30878* (2013.01); *A61F 2002/30881* (2013.01); *A61F 2002/30884* (2013.01); *A61F 2002/30892* (2013.01); *A61F 2002/30985* (2013.01)

(58) Field of Classification Search
CPC .. A61F 2002/30881; A61F 2002/30878; A61F 2002/30827; A61F 2002/30594; A61F 2002/30884; A61F 2002/30011; A61F 2002/2892; A61F 2002/30892; A61F 2002/3092; A61F 2002/3093; A61F 2002/30985; A61F 2002/30784
See application file for complete search history.

(56) References Cited

U.S. PATENT DOCUMENTS

| | | | |
|---|---|---|---|
| 4,795,472 A * | 1/1989 | Crowninshield | A61F 2/30767 623/23.29 |
| 4,842,517 A * | 6/1989 | Kawahara | A61C 8/0012 433/173 |
| 4,938,769 A * | 7/1990 | Shaw | A61F 2/3845 623/20.15 |
| 4,997,445 A * | 3/1991 | Hodorek | A61F 2/30907 623/23.51 |
| 5,387,243 A * | 2/1995 | Devanathan | A61F 2/30734 128/898 |
| 5,534,030 A * | 7/1996 | Navarro | A61F 2/30767 623/17.15 |
| 5,534,032 A * | 7/1996 | Hodorek | A61F 2/389 623/20.32 |
| 5,609,641 A * | 3/1997 | Johnson | A61F 2/389 623/20.32 |
| 5,702,484 A * | 12/1997 | Goymann | A61F 2/30724 623/23.21 |
| 5,716,358 A * | 2/1998 | Ochoa | A61B 17/68 606/301 |
| 5,723,011 A * | 3/1998 | Devanathan | A61F 2/30907 128/898 |
| 6,027,682 A | 2/2000 | Almquist et al. | |
| 6,080,219 A | 6/2000 | Jha et al. | |
| 6,869,448 B2 * | 3/2005 | Tuke | A61F 2/389 623/20.14 |
| 7,537,664 B2 | 5/2009 | O'Neill et al. | |
| 7,597,715 B2 * | 10/2009 | Brown | A61F 2/34 623/22.12 |
| 8,021,432 B2 * | 9/2011 | Meridew | A61F 2/36 623/22.32 |
| 8,266,780 B2 * | 9/2012 | Bollinger | A61F 2/367 29/447 |
| 8,268,099 B2 | 9/2012 | O'Neill et al. | |
| 8,268,100 B2 | 9/2012 | O'Neill et al. | |
| 8,470,047 B2 | 6/2013 | Hazebrouck et al. | |
| 8,556,981 B2 * | 10/2013 | Jones | A61L 27/306 623/20.17 |
| 8,562,348 B2 * | 10/2013 | Collins | A61C 8/0006 433/174 |
| 8,590,157 B2 | 11/2013 | Kruth et al. | |
| 8,888,862 B2 * | 11/2014 | McDonnell | A61F 2/3662 623/23.5 |
| 8,992,703 B2 | 3/2015 | O'Neill et al. | |
| 9,180,010 B2 | 11/2015 | Dong et al. | |
| 9,456,901 B2 | 10/2016 | Jones et al. | |
| 10,307,260 B2 * | 6/2019 | Heldreth | A61F 2/30767 |
| 10,399,147 B2 | 9/2019 | Scott et al. | |
| 2002/0120344 A1 * | 8/2002 | Meulink | A61F 2/30767 623/23.3 |
| 2003/0180171 A1 * | 9/2003 | Artz | C04B 35/63432 419/2 |
| 2004/0236430 A1 * | 11/2004 | Koch | A61F 2/3662 623/23.31 |
| 2009/0216325 A1 | 8/2009 | May et al. | |
| 2010/0298947 A1 * | 11/2010 | Unger | A61F 2/38 623/20.32 |
| 2012/0321878 A1 | 12/2012 | Landon et al. | |
| 2013/0172927 A1 | 7/2013 | Natarajan et al. | |
| 2013/0218284 A1 | 8/2013 | Eickmann et al. | |
| 2013/0325129 A1 | 12/2013 | Huang | |
| 2014/0257507 A1 * | 9/2014 | Wang | A61F 2/30767 623/20.34 |
| 2017/0095337 A1 | 4/2017 | Pasini et al. | |
| 2017/0266007 A1 * | 9/2017 | Gelaude | A61B 34/10 |
| 2018/0228613 A1 | 8/2018 | Jones et al. | |
| 2019/0046322 A1 | 2/2019 | Moore et al. | |
| 2019/0290441 A1 | 9/2019 | Tong et al. | |
| 2019/0298533 A1 | 10/2019 | Kane | |
| 2020/0036011 A1 * | 1/2020 | Numata | A61C 7/20 |
| 2020/0129670 A1 | 4/2020 | Landon et al. | |
| 2021/0085466 A1 | 3/2021 | Tong | |

FOREIGN PATENT DOCUMENTS

| | | |
|---|---|---|
| EP | 2774580 | 9/2014 |
| JP | 2002-038201 A | 2/2002 |
| WO | 96/23459 A1 | 8/1996 |
| WO | 2009/022911 A2 | 2/2009 |

OTHER PUBLICATIONS

Chua et al, Development of a Tissue Engineering Scaffold Structure Library for Rapid Prototyping. Part 1: Investigation and Classification, Int J Adv Manuf Technol, 2003, 21:291-301.

Chua et al, Development of a Tissue Engineering Scaffold Structure Library for Rapid Prototyping. Part 2: Parametric Library and Assembly Program, Int J Adv Manuf Technol, 2003, 21: 302-312.

Hong et al, A New Ti-5Ag Alloy for Customized Prostheses by Three-dimensional Printing (3DPtm), Research Reports, Biomaterials & Bioengineering, J Dent Res 80(3), 2001, 860-863.

Meiners et al, Direct Generation of Metal Parts and Tools by Selective Laser Powder Remelting (SLPR); Fraunhofer Institute for Laser Technoloby (ILT), 1999, 655-662.

Morgan et al, Direct Metal Laser Re-Melting (DMLR) of 316L Stainless Steel Powder, Part 1: Analysis of Thin Wall Structures, Research in Advanced Technologies Group, Faculty of Engineering, The University of Liverpool, UK, 2001, 276-282.

Morgan et al, Direct Metal Laser Re-Melting of 316L Stainless Steel Powder, Part 2: Analysis of Cubic Primitives, Research in Advanced Technologies Group, Faculty of Engineering, The University of Liverpool, UK, 2001, 283-295.

Morgan et al, Experimental investigation of nanosecond pulsed Nd:YAG laser re-melted pre-placed powder beds, Rapid Prototyping Journal, vol. 7, No. 3, 2001, 159-172.

Morgan et al, High density net shape components by direct laser re-melting of single-phase powders, Journal of Materials Science 37 (2002), 3093-3100.

Mullen et al, Selective Laster Melting: A Unit Cell Approach for the Manufacture of Porous, Titanium, Bone In-Growth Constructs, Suitable for Orthopedic Applications. II. Randomized Structures, Journal of Biomedical Materials Research Part B: Applied Biomaterials, Jan. 2010, 178-188.

Pogson et al, The production of copper parts using DMLR, Rapid Prototyping Journal, vol. 9, No. 5, 2003, 334-343.

Ramos et al, Mechanics of the Selective Laser Raster-Scanning Surface Interaction, Department of Mechanical and Metallurgical Engineering, Pontificia Universidad, Chile, Department of Mechanical Engineering, University of Texas at Austin, Aug. 2003, 559-572.

Williams et al, Selective Laser Sintering Part Strength as a Function of Andrew Number Scan Rate and Spot Size, Clemson University, 1996, 10 pages.

(56) References Cited

OTHER PUBLICATIONS

Williams, et al, Advances in modeling the effects of selected parameters on the SLS process, Rapid Prototyping Journal, vol. 4, No. 2, 1998, 90-100.
Wysocki et al, Laser and Electron Beam Additive Manufacturing Methods of Fabricating Titanium Bone Implants, Applied Sciences, 7, 657, 2017, 20 pages.
Yang et al, the design of scaffolds for use in tissue engineering, Part II. Rapid prototyping techniques, Tissue engineering, Feb. 2002; vol. 8(1), 1-11.
Yang et al, The design of scaffolds for use in tissue engineering. Part I. Traditional factors, Tissue engineering, Dec. 2001; vol. 7(6), 679-689.

\* cited by examiner

HYBRID FIXATION FEATURES FOR THREE-DIMENSIONAL POROUS STRUCTURES FOR BONE INGROWTH AND METHODS FOR PRODUCING

This application claims priority to U.S. Provisional App. No. 62/650,790, which was filed on Mar. 30, 2018 and is expressly incorporated herein by reference.

TECHNICAL FIELD

The embodiments disclosed herein are generally directed towards porous metal structures and methods for manufacturing them, and, more specifically, to porous metal structures in medical devices.

BACKGROUND

The embodiments disclosed herein are generally directed towards surface features for three-dimensional porous structures for bone ingrowth and methods for producing said structures.

The field of rapid prototyping and additive manufacturing has seen many advances over the years, particularly for rapid prototyping of articles such as prototype parts and mold dies. These advances have reduced fabrication cost and time, while increasing accuracy of the finished product, versus conventional machining processes, such as those where materials (e.g., metal) start as a block of material, and are consequently machined down to the finished product.

However, the main focus of rapid prototyping three-dimensional structures has been on increasing density of rapid prototyped structures. Examples of modern rapid prototyping/additive manufacturing techniques include sheet lamination, adhesion bonding, laser sintering (or selective laser sintering), laser melting (or selective laser sintering), photopolymerization, droplet deposition, stereolithography, 3D printing, fused deposition modeling, and 3D plotting. Particularly in the areas of selective laser sintering, selective laser melting and 3D printing, the improvement in the production of high density parts has made those techniques useful in designing and accurately producing articles such as highly dense metal parts.

In the field of tissue engineering, a porous three-dimensional biocompatible scaffold is needed to accommodate mammalian cells and promote their three-dimensional growth and regeneration, and thus can be used for example, as implants/prosthetic components or other prostheses. Furthermore, this scaffold, or ingrowth coating, requires sufficient surface texture to promote stable implant-bone interface essential for rapid and effective bone ingrowth. Fixation features (e.g., pegs) with higher fixation strength limit, for example, the implant-to-bone motion and increase opportunity for bony in-growth more than pegs that are not well fixated in the bone.

SUMMARY

According to one aspect of the disclosure, an orthopaedic prosthetic component is disclosed. The orthopaedic prosthetic component comprises a base and a fixation peg extending away from the base to a distal tip. The fixation peg includes a porous three-dimensional structure configured to permit bone in-growth, and the porous three-dimensional structure has an outer surface boundary. The fixation peg includes a plurality of plates attached to the porous three-dimensional structure at the outer surface boundary. Each plate includes a tapered body having an outer wall that faces away from the porous three-dimensional structure and is devoid of any openings.

In some embodiments, the tapered body of each plate may extend longitudinally along the porous three-dimensional structure. Additionally, in some embodiments, the tapered body of each plate may extend from a proximal end to a distal end, and the tapered body of each plate may have a first width at the proximal end and a second width greater than the first width between the proximal end and the distal end.

In some embodiments, the outer wall of each plate may include a concave surface that defines a tapered channel. In some embodiments, each plate is a solid plate that is devoid of any openings or through-holes.

In some embodiments, the plurality of plates may be arranged circumferentially on the porous three-dimensional structure. Additionally, in some embodiments, adjacent plates of the plurality of plates may be spaced apart circumferentially from each other on the porous three-dimensional structure.

In some embodiments, the plurality of plates may be positioned between the distal tip of the fixation peg and the base. Additionally, in some embodiments, the base may include a tibial platform configured to receive a tibial insert. In some embodiments, an elongated stem may extend from the tibial platform to a distal tip. The elongated stem may be configured to be implanted in a surgically-prepared proximal end of a patient's tibia.

In some embodiments, the orthopaedic prosthetic component may further comprise a porous three-dimensional layer attached to a distal surface of the tibial platform. The elongated stem may extend outwardly from the three-dimensional layer, and the fixation peg extends outwardly from the porous three-dimensional layer.

In some embodiments, the tapered body of each plate may extend from a proximal end to a distal end, and the tapered body of each plate may have a first thickness at the distal end and a second thickness greater than the first thickness between the proximal end and the distal end.

In some embodiments, each plate may extend circumferentially around the porous three-dimensional structure. Additionally, in some embodiments, adjacent plates of the plurality of plates may be spaced apart from each other on the porous three-dimensional structure in a proximal-distal direction. In some embodiments, the distal tip of the fixation peg may include a longitudinal slot.

According to another aspect, an orthopaedic prosthetic component comprises a tibial platform configured to receive a tibial insert and a porous three-dimensional structure coupled to the tibial platform. The porous three-dimensional structure is configured to permit bone in-growth. The orthopaedic prosthetic component also comprises an elongated stem extending away from the tibial platform to a distal tip. The porous three-dimensional structure includes a layer coupled to the tibial platform and a plurality of fixation pegs extending from the layer. Each fixation peg includes a portion of the porous three-dimensional structure that has an outer surface boundary. A plurality of plates are attached at the outer surface boundary of each fixation peg. Each plate includes a tapered body having an outer wall that is devoid of any openings.

In some embodiments, the tapered body of each plate may extend longitudinally along the porous three-dimensional structure. Additionally, in some embodiments, the outer wall of each plate may include a concave surface that defines a tapered channel.

In some embodiments, adjacent plates of the plurality of plates may be spaced apart circumferentially from each other on each peg. In some embodiments, adjacent plates of the plurality of plates may be spaced apart from each other on the porous three-dimensional structure in a proximal-distal direction.

According to another aspect, a method for producing an orthopaedic prosthetic component is disclosed. The method comprises depositing and scanning successive layers of metal powders to form a porous three-dimensional structure comprising at least one fixation peg. The at least one fixation peg comprises a porous portion and at least one solid plate positioned on the porous portion.

According to yet another aspect, an orthopaedic implant is disclosed. The implant comprises a porous three-dimensional structure and at least one fixation feature extending past a surface boundary of the porous three-dimensional structure. The porous three-dimensional structure is comprised of a plurality of unit cells. The fixation feature is anchored to a first side of the porous three-dimensional structure and is comprised of a porous portion and a plurality of solid portions positioned on an outside surface of the porous portion.

In some embodiments, the implant further comprises a base that is anchored to a second side of the porous three-dimensional structure.

In some embodiments, the fixation feature is further comprised of a length that is greater than a width.

In some embodiments, the fixation feature is further comprised of a width that is greater than a length.

In some embodiments, the plurality of solid portions extend outwardly from the surface boundary of the porous three-dimensional structure.

In some embodiments, the plurality of solid portions are positioned substantially parallel to the surface boundary of the porous three-dimensional structure.

In some embodiments, the fixation feature is further comprised of a porous tip portion distal to the porous three-dimensional structure.

In some embodiment, the implant is further comprised of a plurality of fixation features.

In some embodiments, the porous portion further includes a plurality of scallops. In some embodiments, each of the plurality of solid portions occupy a respective scallop. In some embodiments, each of the plurality of scallops is comprised of a distal region that is larger than a proximal region.

In some embodiments, at least one of the plurality of solid portions is attached to a porous portion. In some embodiments, the plurality of solid portions tapers in the distal direction. In some embodiments, each of the plurality of solid portions is attached to a porous portion. In some embodiments, each of the plurality of solid portions tapers in a distal direction. In some embodiments, the thickness of each respective solid portion is less than the solid portion immediately proximal.

In another aspect, an orthopaedic implant is disclosed. The implant comprises a porous three-dimensional structure including at least one fixation feature. The one fixation feature comprises a porous portion having an interior, at least one solid portion and at least one slot that is partially located on the interior of the porous portion.

In some embodiments, the at least one solid portion is positioned on an outside surface of the porous portion.

In some embodiments, the implant is further comprised of a base that is anchored to a second side of the porous three-dimensional structure.

In some embodiments, the fixation feature is comprised of a width that is greater than the length.

In some embodiments, the fixation feature is comprised of a length that is greater than the width.

In some embodiments, the at least one solid portion is positioned substantially perpendicular to the surface boundary of the porous three-dimensional structure.

In some embodiments, the at least one solid portion extends to a tip region of the at least one fixation feature that is distal to the porous three-dimensional structure.

In some embodiments, the implant is further comprised of a plurality of fixation features.

In some embodiments, the at least one solid portion includes at least one barb that tapers in the distal direction. In some embodiments, the at least one solid portion includes a plurality of barbs. In some embodiments, the thickness of each respective barb is less than the barb immediately proximal.

In some embodiments, the at least one solid portion is attached to the porous portion.

In some embodiments, the at least one solid portion tapers in the distal direction.

In some embodiments, the implant is comprised of a plurality of solid portions. In some embodiments, each of the plurality of solid portions attaches to the porous portion. In some embodiments, each of the plurality of solid portions tapers in the distal direction. In some embodiments, each of the plurality of solid portions includes at least one barb that tapers in the distal direction.

In some embodiments, the at least one slot provides an opening at a tip region of the at least one fixation feature.

In some embodiments, the implant is comprised of a plurality of slots.

In another aspect, a method for producing an orthopaedic implant is disclosed. The method comprises depositing and scanning successive layers of metal powders to form a porous three-dimensional structure comprising a plurality of unit cells and to form at least one fixation feature that extends beyond a surface boundary of the porous three-dimensional structure. The at least one fixation feature is anchored to a first side of the porous three-dimensional structure and is comprised of a porous portion having an interior, at least one solid portion and at least one slot at least partially located on the interior of the porous portion.

In some embodiments, the method further comprises providing a base and anchoring a second side of the porous three-dimensional structure to the base.

In yet another aspect, a method for producing a porous three-dimensional structure is disclosed. The method comprises depositing and scanning successive layers of metal powders with a beam to form a porous three-dimensional structure comprising a plurality of unit cells and to form at least one fixation feature that extends beyond a surface boundary of the porous three-dimensional structure. The at least one fixation feature is anchored to a first side of the porous three-dimensional structure and comprises a porous portion and a plurality of solid portions positioned on an outside surface of the porous portion.

In some embodiments, the method further comprises providing a base and anchoring a second side of the porous three-dimensional structure to the base.

In some embodiments, the beam is an electron beam.

In some embodiments, the beam is a laser beam.

In some embodiments, the metal powders are melted to form the porous three-dimensional structure.

In some embodiments, the metal powders are sintered to form the porous three-dimensional structure.

In some embodiments, the successive layers of metal powders are deposited onto a solid base.

In another aspect, a method for producing a porous three-dimensional structure is disclosed. The method comprises applying a stream of metal particles at a predetermined velocity onto a base to form a porous three-dimensional structure and to form at least one fixation feature that extends beyond a surface boundary of the porous three-dimensional structure. The porous three-dimensional structure is comprised of a plurality of unit cells. The fixation feature is anchored to a first side of the porous three-dimensional structure and is comprised of a porous portion and a plurality of solid portions positioned on an outside surface of the porous portion.

In some embodiments, the method further comprises anchoring a second side of the porous three-dimensional structure to the base.

In some embodiments, the predetermined velocity is a critical velocity required for the metal particles to bond upon impacting the base. In some embodiments, the critical velocity is greater than about 340 m/s.

In some embodiments, the method further comprises applying a laser beam at a predetermined power setting onto an area of the base where the stream of metal particles is impacting.

In another aspect, a method for producing a porous three-dimensional structure is disclosed. The method comprises introducing a continuous feed of metal wire onto a base surface and applying a beam at a predetermined power setting to an area where the metal wire contact the base surface to form a porous three-dimensional structure and to form at least one fixation feature that extends beyond a surface boundary of the porous three-dimensional structure. The porous three-dimensional structure is comprised of a plurality of unit cells. The fixation feature is anchored to a first side of the porous three-dimensional structure and comprises a porous portion and a plurality of solid portions positioned on an outside surface of the porous portion.

In some embodiments, the method further comprises anchoring a second side of the porous three-dimensional structure to the base.

In some embodiments, the beam is an electron beam.

In some embodiments, the beam is a laser beam.

In yet another aspect, a method for producing a porous three-dimensional structure is disclosed. The method comprises introducing a continuous feed of polymer material embedded with metal elements onto a base surface, applying heat to an area where the polymer material contacts the base surface to form porous three-dimensional structure and to form at least one fixation feature that extends beyond a surface boundary of the porous three-dimensional structure. The porous three-dimensional structure is comprised of a plurality of unit cells. The fixation feature is anchored to a first side of the porous three-dimensional structure and comprises a porous portion and a plurality of solid portions positioned on an outside surface of the porous portion.

In some embodiments, the method further comprises anchoring a second side of the porous three-dimensional structure to the base.

In some embodiments, the method further includes scanning the porous three-dimensional structure with a beam to burn off the polymer material.

In some embodiments, the heat is applied using a heating element. In some embodiments, the heating element is part of a furnace system.

In another aspect, a method for producing a porous three-dimensional structure is disclosed. The method comprises introducing a metal slurry through a nozzle onto a base surface to form a porous three-dimensional structure and at least one fixation feature that extends beyond a surface boundary of the porous three-dimensional structure. The porous three-dimensional structure is comprised of a plurality of unit cells. The fixation feature is anchored to a first side of the porous three-dimensional structure and comprises a porous portion and a plurality of solid portions positioned on an outside surface of the porous portion.

In some embodiments, the method further comprises anchoring a second side of the porous three-dimensional structure to the base.

In yet another aspect, a method for producing a porous three-dimensional structure is disclosed. The method comprises introducing successive layers of molten metal onto a base surface to form a porous three-dimensional structure and at least one fixation feature that extends beyond a surface boundary of the porous three-dimensional structure. The porous three-dimensional structure is comprised of a plurality of unit cells. The fixation feature is anchored to a first side of the porous three-dimensional structure and is comprised of a porous portion and a plurality of solid portions positioned on an outside surface of the porous portion.

In some embodiments, the method further comprises anchoring a second side of the porous three-dimensional structure to the base.

In another aspect, a method for producing a porous three-dimensional structure is disclosed. The method comprises depositing and binding successive layers of metal powders with a binder material to form a porous three-dimensional structure and at least one fixation feature that extends beyond a surface boundary of the porous three-dimensional structure. The porous three-dimensional structure is comprised of a plurality of unit cells. The fixation feature is anchored to a first side of the porous three-dimensional structure and is comprised of a porous portion and a plurality of solid portions positioned on an outside surface of the porous portion.

In some embodiments, the method further comprises providing a base and anchoring a second side of the porous three-dimensional structure to the base.

In some embodiments, the method further includes sintering or melting the bound metal powder with a beam. In some embodiments, the beam is an electron beam. In some embodiments, the beam is a laser beam.

In some embodiments, the method further includes sintering or melting the bound metal powder with a heating element.

In yet another aspect, a method for producing a porous three-dimensional structure is disclosed. The method comprises depositing droplets of a metal material onto a base surface and applying heat to an area where the metal material contacts the base surface to form a porous three-dimensional structure and at least one fixation feature that extends beyond a surface boundary of the porous three-dimensional structure. The porous three-dimensional structure is comprised of a plurality of unit cells. The fixation feature is anchored to a first side of the porous three-dimensional structure and is comprised of a porous portion and a plurality of solid portions positioned on an outside surface of the porous portion.

In some embodiments, the method further comprises anchoring a second side of the porous three-dimensional structure to the base.

In some embodiments, the heat is applied with an electron beam.

In some embodiments, the heat is applied with a laser beam.

In some embodiments, the metal material is a metal slurry embedded with metallic elements.

In some embodiments, the metal material is a metal powder.

BRIEF DESCRIPTION OF THE DRAWINGS

For a more complete understanding of the principles disclosed herein, and the advantages thereof, reference is now made to the following descriptions taken in conjunction with the accompanying drawings, in which.

DETAILED DESCRIPTION

Figure 1:
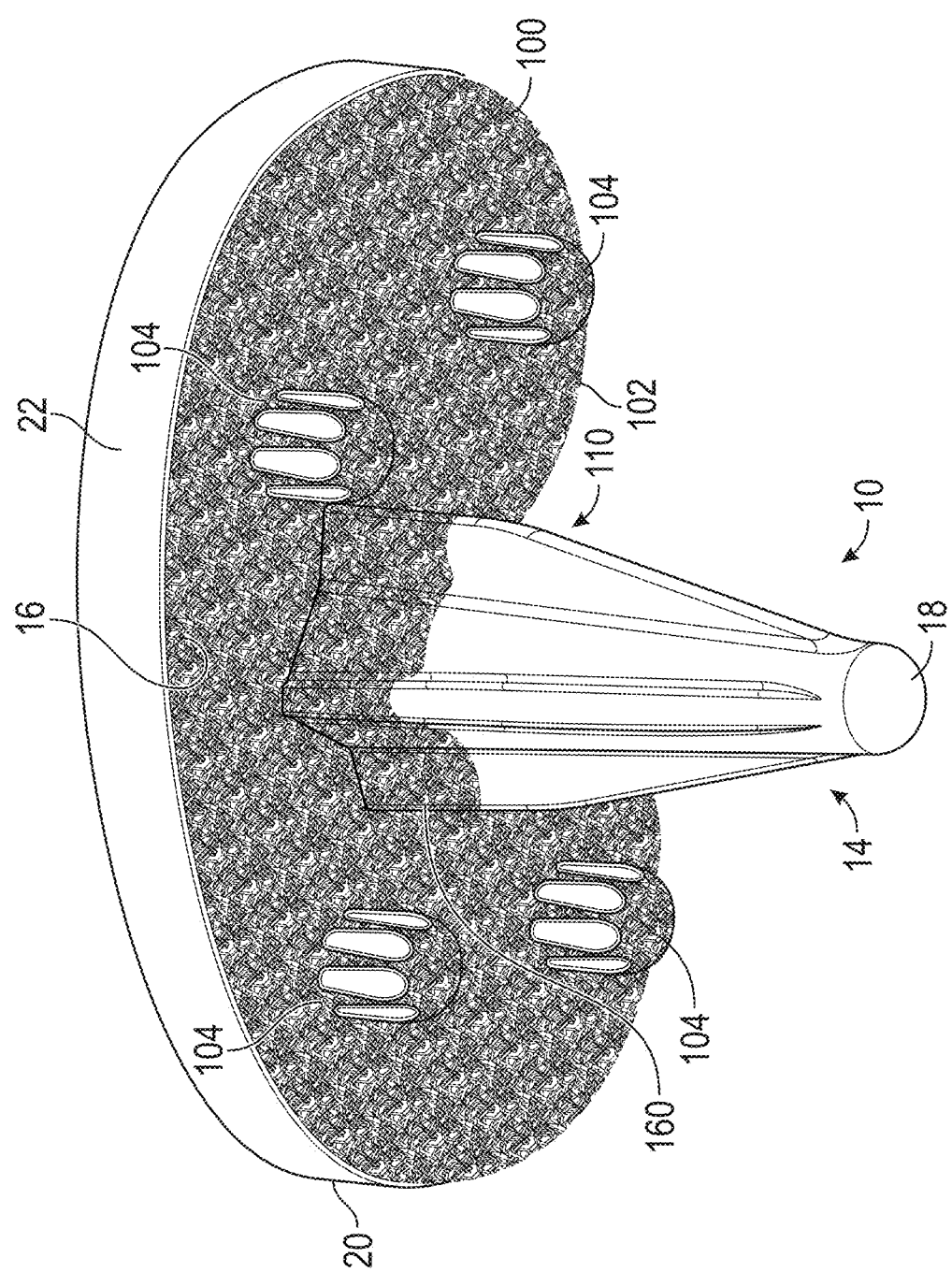
FIG. 1 is a perspective view of an orthopaedic prosthetic component.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a base, etc.) can be "on," "attached to," "connected to," or "coupled to" another element regardless of whether the one element is directly on, attached to, connected to, or coupled to the other element, there are one or more intervening elements between the one element and the other element, or the two elements are integrated as a single piece. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

As used herein, "bonded to" or "bonding" denotes an attachment of metal to metal due to a variety of physico-chemical mechanisms, including but not limited to: metallic bonding, electrostatic attraction and/or adhesion forces.

Unless otherwise defined, scientific and technical terms used in connection with the present teachings described herein shall have the meanings that are commonly understood by those of ordinary skill in the art.

The present disclosure relates to porous three-dimensional metallic structures and methods for manufacturing them for medical applications. As described in greater detail below, the porous metallic structures promote hard or soft tissue interlocks between prosthetic components implanted in a patient's body and the patient's surrounding hard or soft tissue. For example, when included on an orthopaedic prosthetic component configured to be implanted in a patient's body, the porous three-dimensional metallic structure can be used to provide a porous outer layer of the orthopaedic prosthetic component to form a bone in-growth structure. Alternatively, the porous three-dimensional metallic structure can be used as an implant with the required structural integrity to both fulfill the intended function of the implant and to provide interconnected porosity for tissue interlock (e.g., bone in-growth) with the surrounding tissue.

In accordance with various embodiments, an orthopaedic prosthetic component is provided, the prosthetic component including a base, a porous three-dimensional structure, and at least one surface feature (hereinafter referred to as an engagement stud) extending past a surface boundary of the porous three-dimensional structure. The porous structure can include a plurality of unit cells.

The orthopaedic implant/prosthetic component, by design, can be a surgical implant configured for implantation into a patient's bone. For example, as shown in FIG. 1, an orthopaedic prosthetic component 10 is a tibial tray of a total knee arthroplasty prosthesis. The component 10 includes a platform 12 having a stem 14 extending away from its lower surface 16. The tibial stem 14 extends to a distal tip 18 and is configured to be implanted into a surgically-prepared proximal end of a patient's tibia (not shown). The platform 12 also has an upper surface 20 positioned opposite the lower surface 16 and a curved outer wall 22 that extends between the surfaces 16, 20. In the illustrative embodiment, the curved outer wall 22 is shaped to correspond to the outer edge of a surgically-prepared surface on the proximal end of the patient's tibia. The platform 12 also has various engagement features (not shown) attached to the upper surface 20, which are configured to engage an insert or bearing of the total knee arthroplasty prosthesis. Exemplary engagement features, as well as exemplary other components of the knee arthroplasty prosthesis, are shown and described in U.S. Pat. No. 8,470,047, which is expressly incorporated herein by reference.

The platform 12 of the component 10 is constructed with a biocompatible metal, such as a cobalt chrome or titanium alloy, although other materials may also be used. As shown in FIG. 1, the component 10 includes a three-dimensional ingrowth body 100, which is attached to the lower surface 16 of the platform 12 such that the platform 12 provides a base for the ingrowth body 100. The ingrowth body 100 includes a porous three-dimensional structure 110 that is configured to promote bone ingrowth for permanent fixation, as described in greater detail below.

In the illustrative embodiment, the ingrowth body 100 includes a layer or plate 102 attached to the lower surface 16 of the platform 12 and a number of pegs 104 that extend outwardly from the plate 102. The ingrowth body 100 is also attached to the stem 14, which extends outwardly through the layer 102 to its distal tip 18. It should be appreciated that although a tibial prosthetic component is shown, the various porous structures described herein (including engagement stud structures described herein) can be incorporated into various orthopaedic implant designs such that the design of the implant will not impact the ability to use any of the various embodiments of engagement studs discussed herein. For example, the porous structures described herein may be included in a femoral prosthetic component similar to the femoral component shown in U.S. Pat. No. 8,470,047 or on a patella component shaped to engage the femoral prosthetic component. The porous structures may also be included in other orthopaedic implant designs, including prosthetic components for use in a hip or shoulder arthroplasty surgery.

It should be noted, for the preceding and going forward, that a base can be any type of structure capable of, for example, contacting, supporting, connecting to or with, or anchoring to or with components of various embodiments herein. Bases can include, for example, a metal or non-metal platform, a metal or non-metal tray, a metal or non-metal baseplate, a metal or non-metal structure that sits on a tray, and so on.

Figure 2:
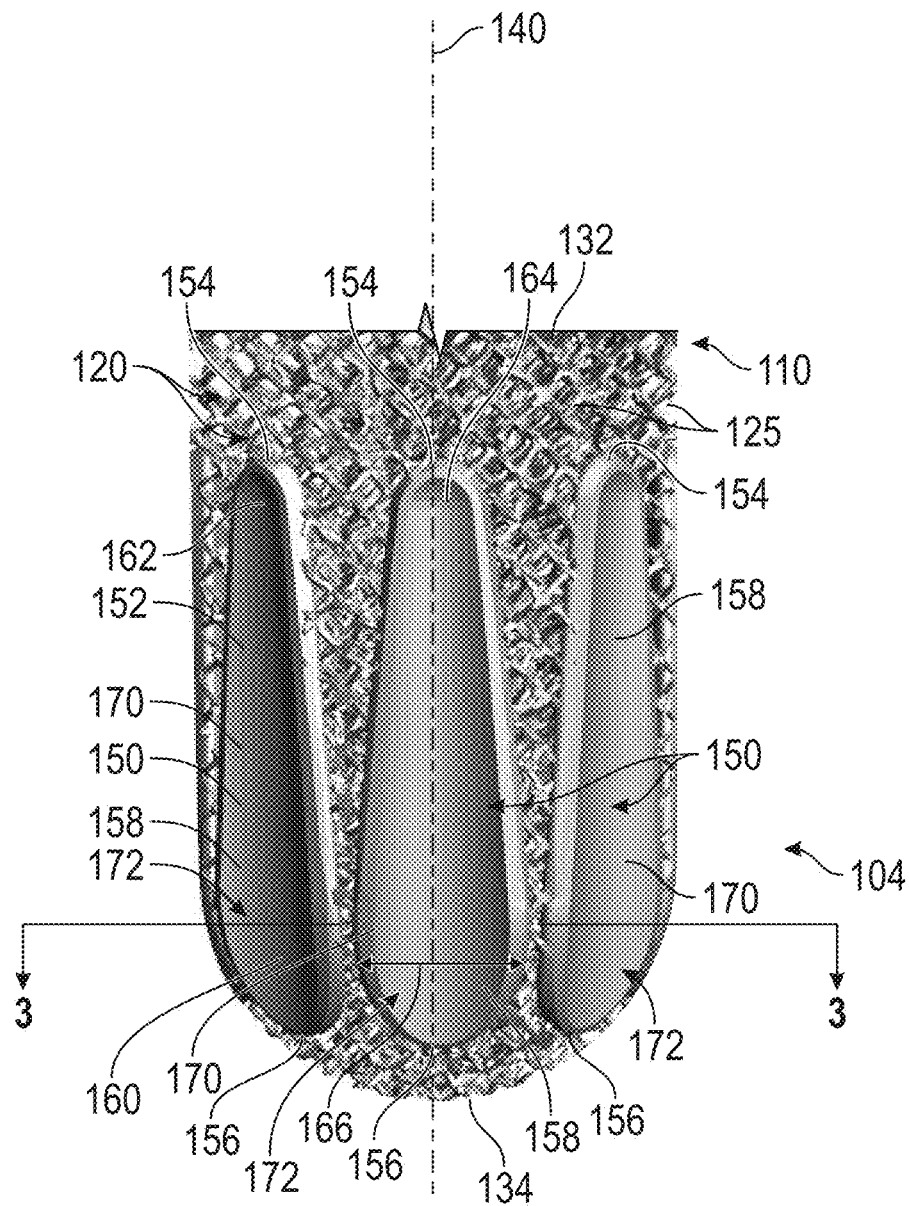
FIG. 2 is an elevation view of a fixation feature of the orthopaedic prosthetic component of FIG. 1.

Referring now to FIG. 2, one fixation peg 104 is shown in greater detail. In the illustrative embodiment, each of the pegs 104 has an identical configuration. The ingrowth body 100 (and hence each peg 104) includes a porous three-dimensional structure 110 that includes a plurality of unit cells 120, each made up multiple struts 125. The plurality of unit cells 120 are provided in repeating patterns to form the structure 110, which has an outer surface boundary 130. The unit cells 120 define pores or voids that permit bone ingrowth after the orthopaedic prosthetic component 10 is implanted in the patient's bone, thereby promoting fixation between the component 10 and the surrounding bone tissue.

Each fixation peg 104 extends from a proximal end 132 attached to the layer 102 of the ingrowth body 100 to a distal end 134. In the illustrative embodiment, the fixation pegs 104 and the layer 102 are formed as a single monolithic porous component. It should be appreciated that in other embodiments the layer 102 may be formed separately from one or more of the fixation pegs 104 and later assembled with the peg(s). It should also be appreciated that one or more of the fixation pegs may be attached directed to the platform 16 and extend through the layer 102.

Figure 3:
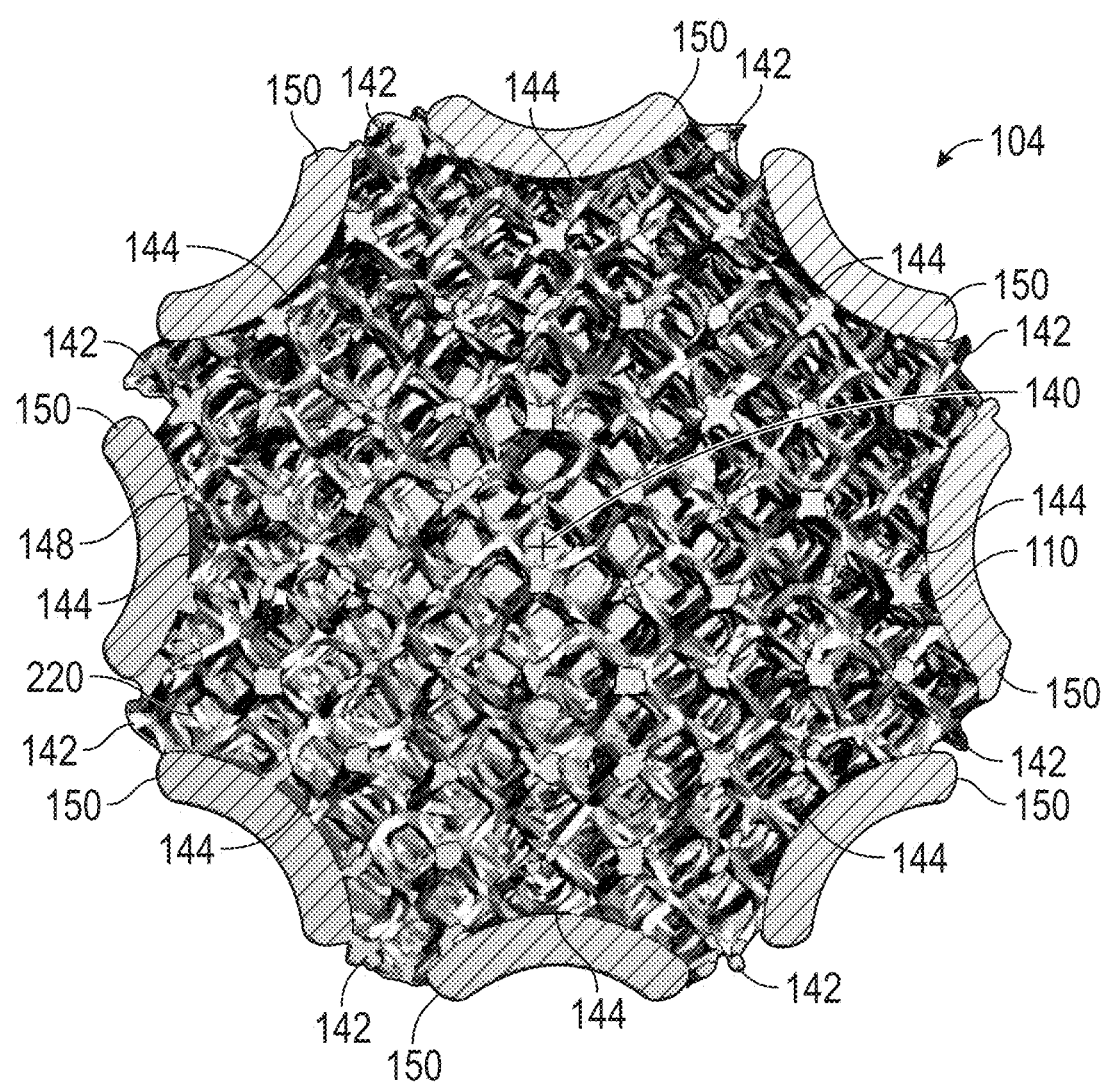
FIG. 3 is a cross-sectional plan view of the fixation feature of FIG. 2 taken along the line 3-3 in FIG. 2.

Each fixation peg 104 extends along a longitudinal axis 140 between the ends 132, 134. As shown in the cross-section of FIG. 3, the outer surface boundary 130 of each peg 104 extends circumferentially around the longitudinal axis 140. In the illustrative embodiment, the outer surface boundary 130 includes a convex section 142 and a number of concave sections 144 that define grooves or channels 148 within the convex section 142. The fixation peg 104 includes a plurality of plates 150, which are attached at the surface boundary 130 within the grooves and are configured to reduce bone abrasion, as described in greater detail below. In other embodiments, the profile of the surface boundary may be more or less uneven than the illustrative embodiment to receive plates of other designs.

In the illustrative embodiment, each groove 148 has a scallop-shape that is tapered. Each of the plurality of plates 150 occupies a respective scallop. Each of the grooves 148 comprises a distal region and proximal region, wherein a portion of the distal region is larger than the proximal region. Alternatively, one or more of the plurality of grooves can comprise a distal region and proximal region, wherein the distal region is smaller than the proximal region.

The plates 150 are arranged circumferentially on the surface boundary 130 of the porous three-dimensional structure 110 of each fixation peg 104. In the illustrative embodiment, the plates 150 are spaced apart from one another by the porous three-dimensional structure 110. Returning to FIG. 2, each plate 150 has a tapered body 152 that extends along the longitudinal axis 140 from a proximal end 154 to a distal end 156. The tapered body 152 of each plate 150 has an outer wall 158 that faces away from the porous three-dimensional structure 110. In the illustrative embodiment, the outer wall 158 is devoid of any openings, and the tapered body 152 is a solid material without any through-holes. It should be appreciated that in other embodiments portions of the outer wall 158 may include openings or through-holes depending on the configuration of the plate and the orthopaedic application.

Each tapered body 152 comprises a distal region 160 including the distal end 156 and a proximal region 162 including the proximal end 154, wherein the distal region includes a portion that is larger than the proximal region. Alternatively, the occupying solid portions can comprise a distal region and proximal region, and the distal region includes a portion that is smaller than the proximal region. As shown in FIG. 2, each tapered body 152 has a width 164 in the proximal region 162 (illustratively at the proximal end 154) and tapers to another, larger width 166 in the distal region 160 (but illustratively between the ends 154, 156).

The outer wall 158 of each tapered body 152 includes a concave surface 170 that defines a channel 172 that is tapered to correspond to the tapering of the body 152. Each channel 172 has an open distal end to facilitate insertion of the peg 104 into a patient's bone. It should be appreciated that in other embodiments channels 172 may have different configurations. As shown in FIG. 2, the distal end 156 of each plate 150 is positioned proximal of the distal tip 134 of each fixation peg 104 such that the plates are positioned between the distal tip 156 and the platform 12 of the orthopaedic prosthetic component. It should be appreciated that in other embodiments the distal end of the plate may be positioned at the distal tip such that they are aligned in a distal plane.

In various embodiments, and as stated above, the solid material can be a metal or non-metal, and the types of metal can include, but are not limited to, titanium, titanium alloys, stainless steel, cobalt chrome alloys, tantalum or niobium. Non-metal examples include, for examples, ceramic materials (e.g., titanium nitride) and carbon materials (e.g., silicon carbide).

By providing a combination of solid components and porous components, the fixation pegs are configured to reduce bone abrasion and increase fixation strength, while still having the porous structure necessary for promoting bone in-growth and also allowing, as needed, for ease of revision (e.g., cutting through the pegs).

Figure 9B:
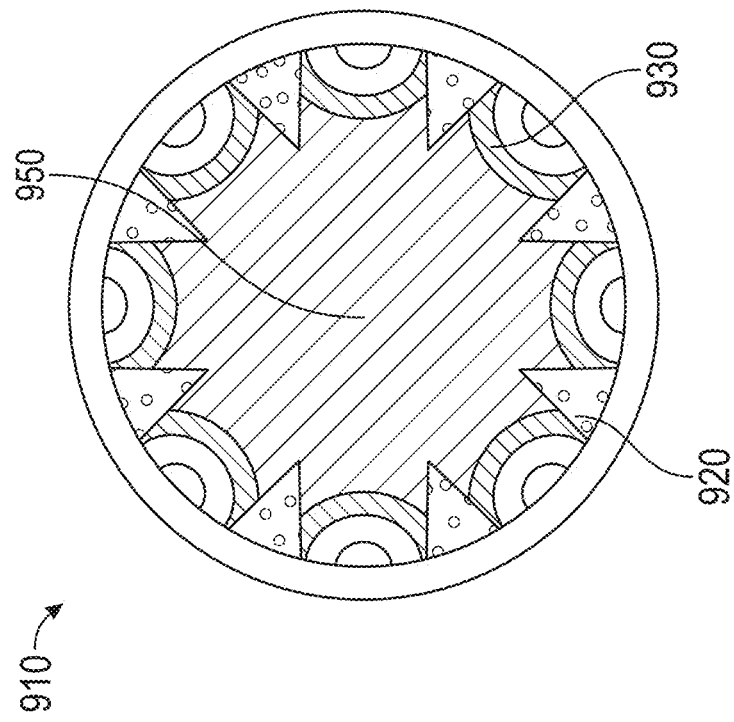
FIGS. 9A and 9B illustrate a cross sectional view of a fixation feature, in accordance with various embodiments.
Figure 9A:
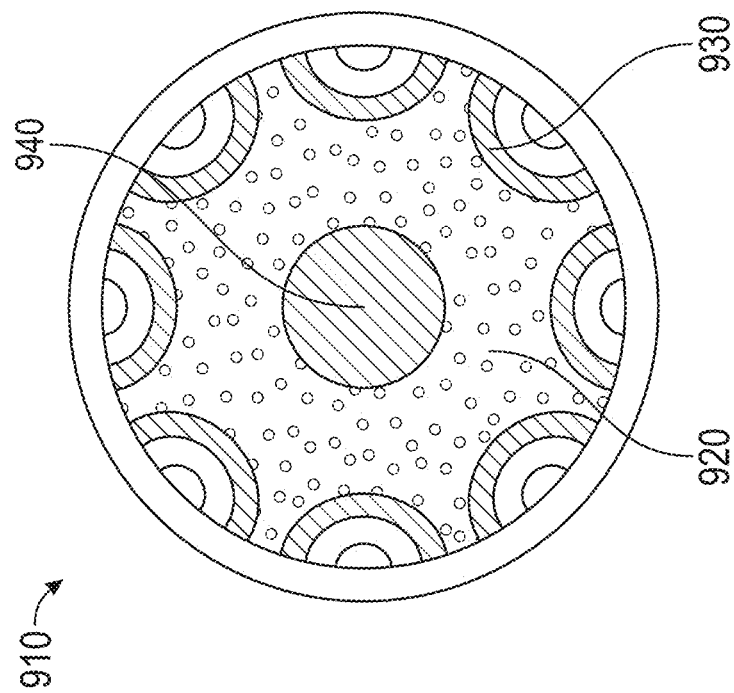

As described above, each fixation peg 104 has a porous structure with solid portions positioned at the surface boundary of the porous structure. It should be appreciated that in other embodiments the fixation peg or feature may have a solid core. For example, as shown in FIG. 9A, a fixation peg 910 has a solid core embedded therein. In FIG. 9A, the fixation feature 910 comprises a porous portion 920 and a plurality of solid plates 930 (or a plurality of solid portions 930). The porous portion 920 furthers include a core 940 of solid material. In FIG. 9B, the porous portion 930 is substantially replaced by a solid core 950. Providing such a solid core, in either case, may potentially provide additional strength to the fixation feature overall to withstand the stress of being embedded in tissue such as bone or for cleaning purposes as needed.

Figure 4:
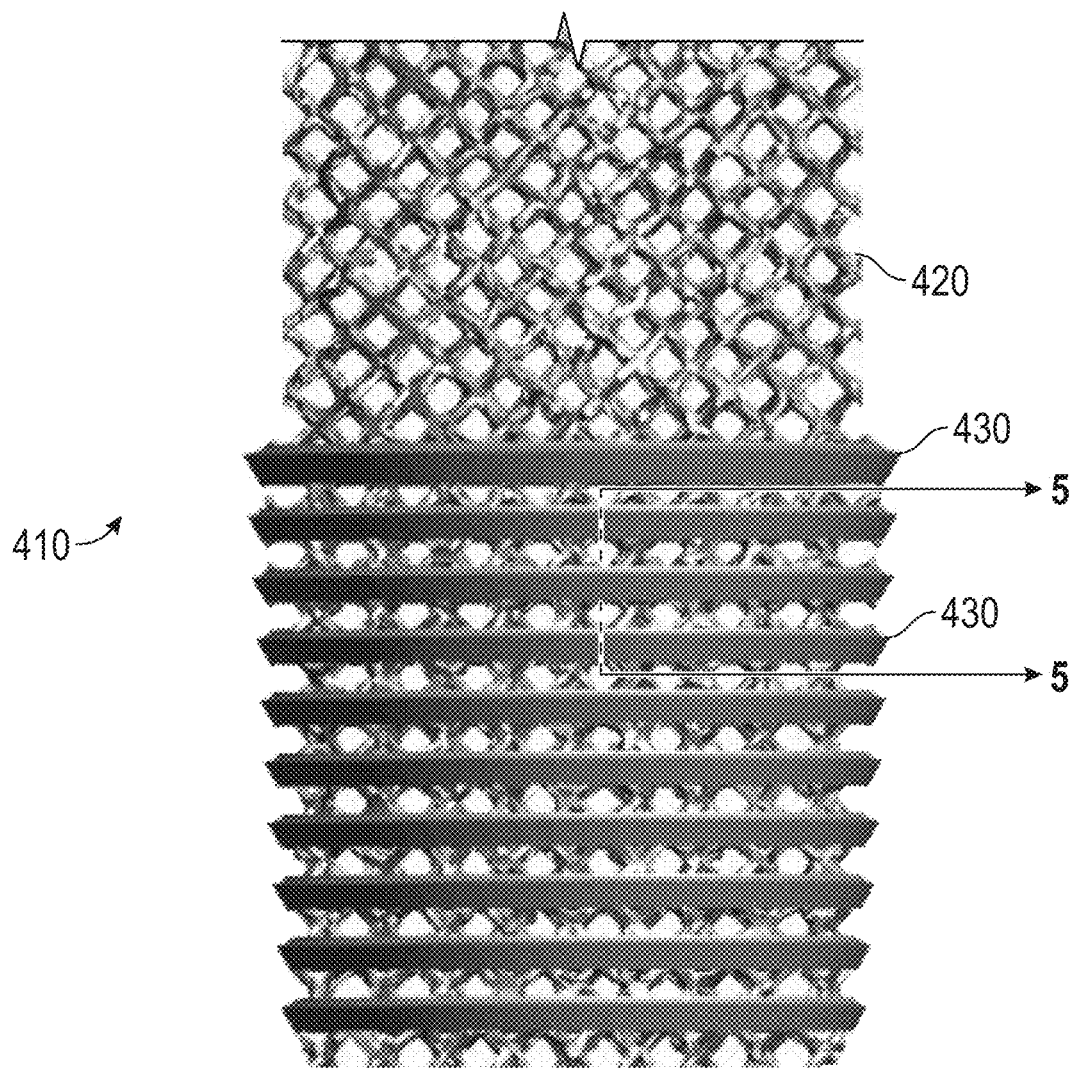
FIG. 4 is an elevation view of another fixation feature for the orthopaedic prosthetic component of FIG. 1.
Figure 5:
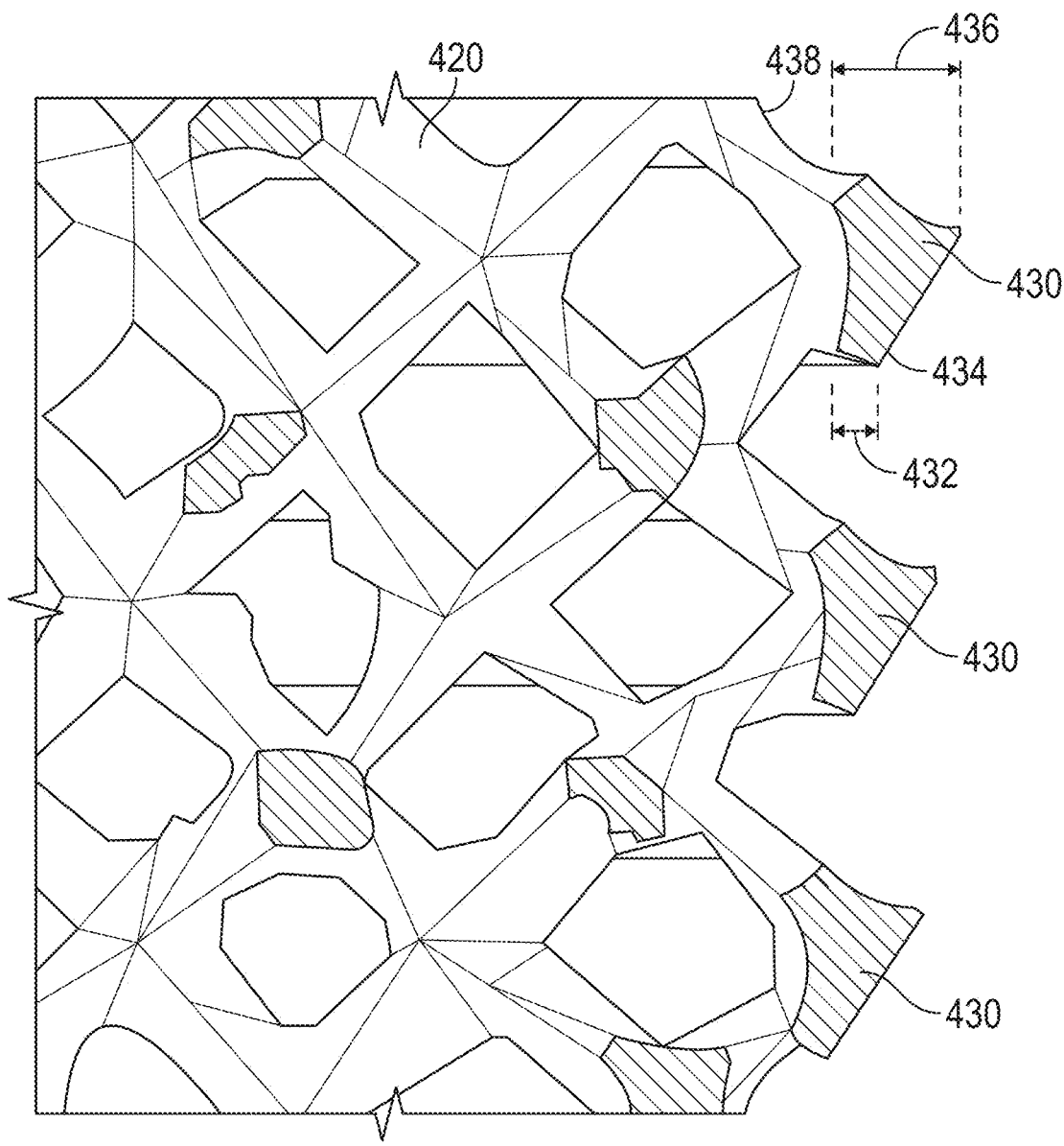
FIG. 5 is a cross-sectional view of a portion of the fixation feature of FIG. 4 taken along the line 5-5 in FIG. 4.
Figure 6:
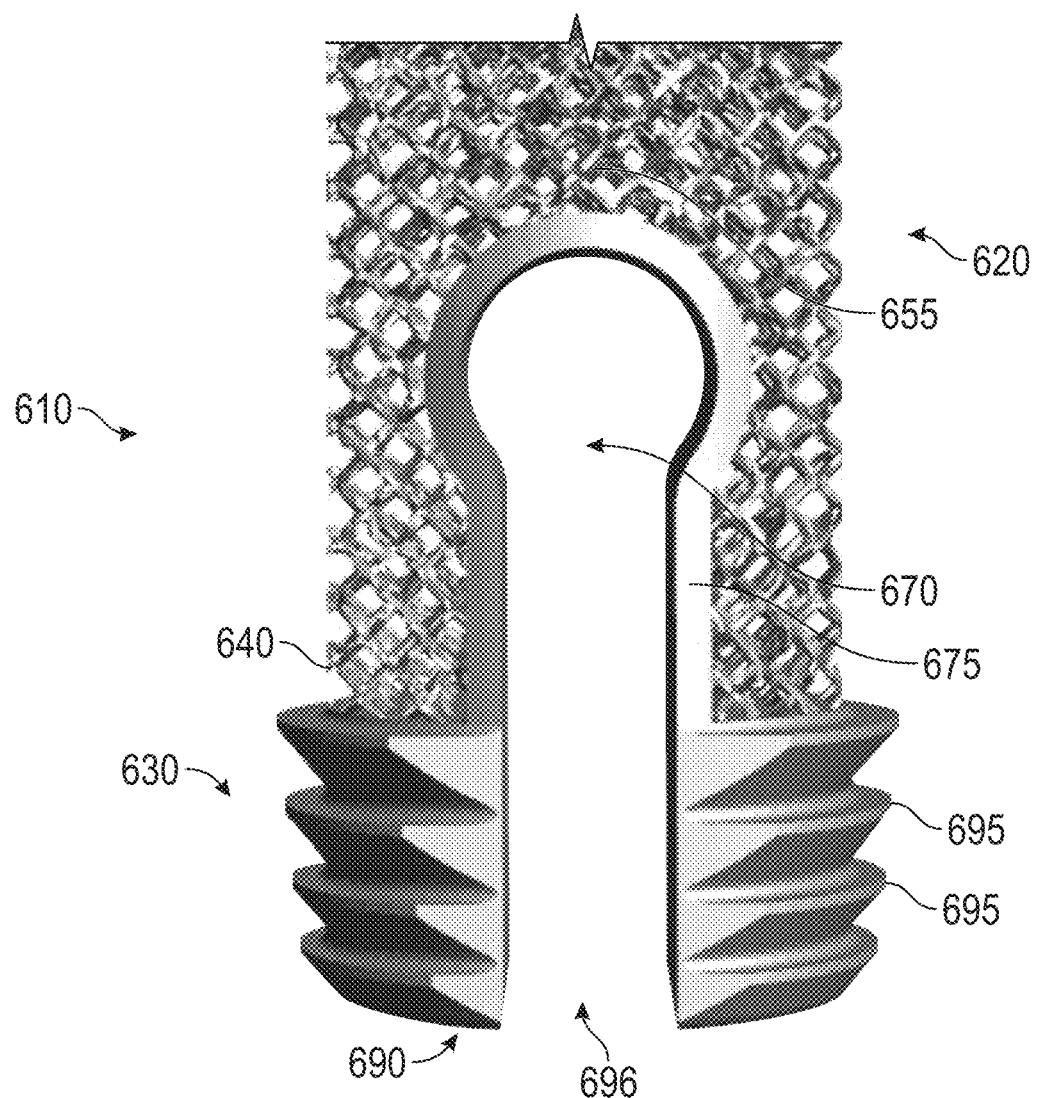
FIG. 6 is an elevation view of another fixation feature for the orthopaedic prosthetic component of FIG. 1.

Referring now to FIGS. 4-6, other examples of fixation features are illustrated, in accordance with various embodiments. In FIGS. 4 and 5, a fixation feature 410 (illustratively another fixation peg) is provided, with the feature 410 comprising a porous three-dimensional structure or portion 420 and at least one solid plate or portion 430. In various embodiments, and as illustrated in FIG. 4, the fixation feature 410 can comprise a plurality of solid portions 430. At least one of the plurality of solid portions can be attached to a surface of the porous portion 420. In FIG. 4, each of the plurality of solid portions 430 is attached to a porous portion 420.

As shown in FIG. 5, each of the plurality of solid portions 430 tapers in the distal direction such that the thickness of each respective solid portion is less than the solid portion immediately proximal. In other words, as shown in FIG. 5, each solid portion 430 has a thickness 432 at its distal end 434 and another, greater thickness 436 proximal of the distal end 434 (illustratively between the distal end 434 and the proximal end 438 of the portion 430). This representative thickness difference between succeeding solid portions presents an overall tapering effect across the solid portions take together, as illustrated, for example, by the successive narrowing of solid portions 430 as fixation feature 410 proceeds distally.

As shown in FIGS. 4-5, each of the solid plates or portions 430 extend circumferentially around the porous portion 420. Adjacent portions 430 of the plurality of portions 430 are spaced apart from each other on the porous portion 420 in a proximal-distal direction.

By providing a design similar to that illustrated, for example, in FIGS. 4 and 5, the solid portions can reduce bone abrasion and increase hoop stresses in the bone. However, with the porous portion, the fixation feature provides regions for bone in-growth and ease of revision. Moreover, by providing designs with a tapering solid portion or plurality of solid portions, the most distal portion of the solid portion may provide a cutting path into the bone that would not disturb bone needed to secure subsequent regions of the solid portion (or subsequent solid portions of the plurality of solid portions).

Referring now to FIG. 6, another fixation feature (hereinafter feature 610) is provided. The fixation feature 610 extends from a layer of a porous three-dimensional structure 660 attached to the platform of the tibial prosthetic component. The fixation feature 610, like the pegs and features of FIGS. 1-5, is configured to engage a patient's bone. Similar to the pegs 104 described above, the fixation feature 610 may be part of a porous three-dimensional structure attached to a solid platform. In such embodiments, a second side 680 of porous three-dimensional structure 660 may be anchored to the platform. Additionally, the fixation feature 610 may be one of a number of fixation features 610. It should also be appreciated that the porous structure 660 can be a solid, or substantially solid, structure. As shown in FIG. 6, each fixation feature 610 includes a porous portion 620 that is anchored to a first side of the layer of structure 660. The porous portion 620 has a plurality of voids or openings that extend through the porous portion 620 and open into an interior 655.

The fixation feature 610 extends to a distal tip 690, and a solid portion 630 is positioned at the distal tip 690 on an outside surface 640 of the porous portion 620. In accordance with various embodiments, and as illustrated for example in FIG. 6, the solid portion includes a number of plates or barbs 695 that are positioned substantially perpendicular to the surface boundary of the porous portion 620. Each barb 695 illustratively tapers in the distal direction (e.g., towards distal tip 690 of fixation feature 610). As shown in FIG. 6, the thickness of each respective barb is less than the barb immediately proximal, and this representative thickness difference between succeeding barbs presents an overall tapering effect across the solid portion 630 by the narrowing of solid portion 630 as fixation feature 610 proceeds distally towards tip region 690. Thus, the at least one solid portion can taper in the distal direction. In other embodiments, the solid portion 630 may not taper. It should also be appreciated that in other embodiments the solid portion 630 may include additional or fewer barbs 695. As illustrated in FIG. 6 for example, the solid portion 630 surrounds the porous portion 620.

The fixation feature 610 also includes an elongated slot 670 that extends from an opening 696 at the distal tip 690. As shown in FIG. 6, the elongated slot 670 extends through the interior 655 of the porous portion 620. The solid portion 630 illustratively includes an inside surface 675 that defines the slot 670. In other embodiments, the elongated slot 670 may be defined by a solid portion separate from the barbs 695. It should also be appreciated that in other embodiments the inside surface 675 may be porous or partially porous.

In accordance with various embodiments, the fixation feature can further comprise a length and a width, wherein the length is greater than the width (as illustrated in FIG. 6). The fixation feature can further comprise a length and a width, wherein the width is greater than the length.

As stated above, in various embodiments, the fixation feature can comprise a plurality of solid portions. Each of the plurality of solid portions can surround the porous portion. Each of the plurality of solid portions can taper in the distal direction. Each of the plurality of solid portions can include at least one barb, wherein the at least one barb tapers in the distal direction.

By providing a fixation feature with a slot as illustrated, for example, in FIG. 6, the fixation feature can deflect during fixation feature insertion to help prevent bone abrasion. The porous portion assists in providing the low modulus necessary for deflection of the fixation features, or more specifically the barbs on the solid portion, while also allowing for sufficient bone in-growth and ease of revision. It should also be noted that, while FIG. 6 illustrates a single slot, a plurality of slots could be used (e.g., 3 to 4 slots) to minimize any directionality of the slotted design.

Figure 7:
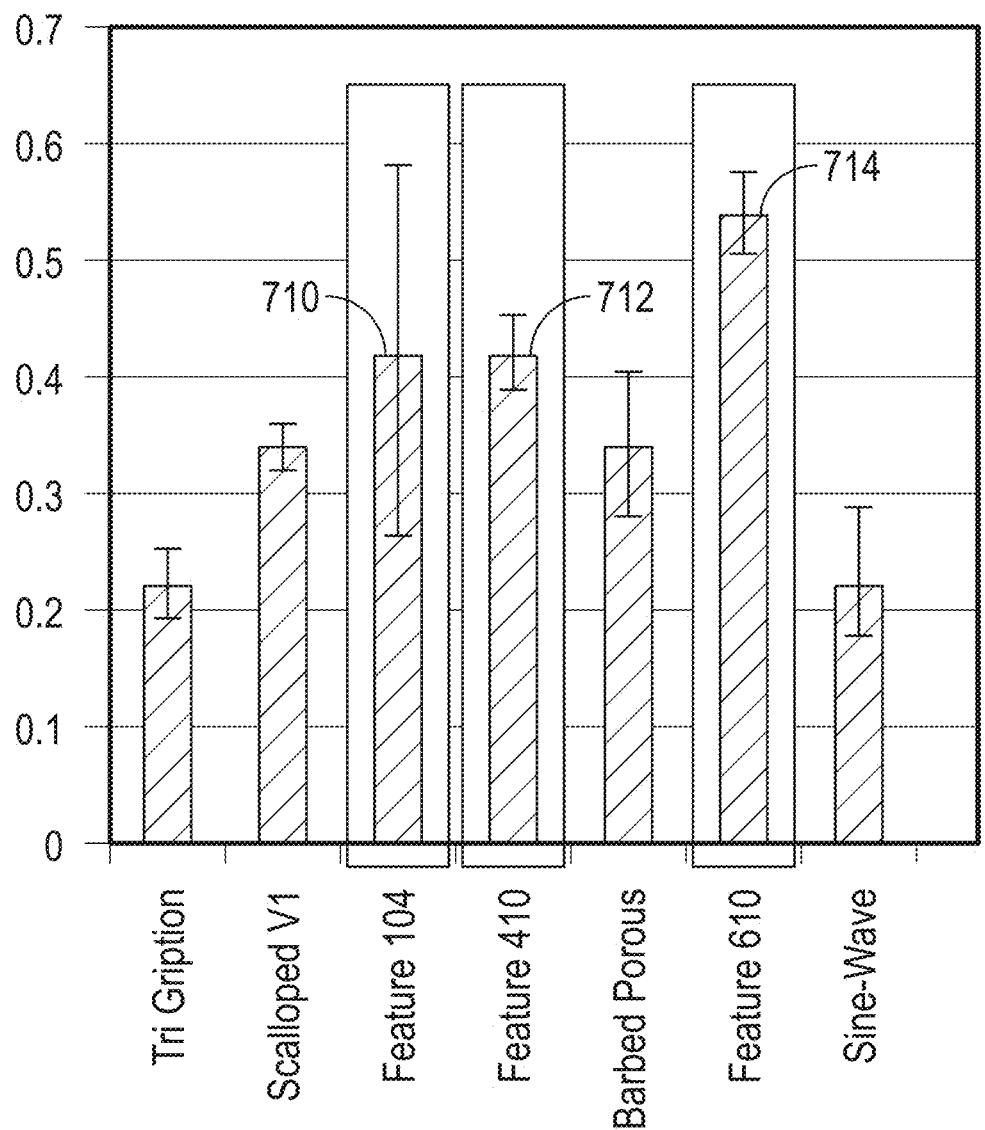
FIG. 7 depicts a chart of the ratio of extraction to insertion force for various features, in accordance with various embodiments.

Referring now to FIG. 7, a chart 700 is provided to show extraction/insertion force ratio results from fixation feature pull-out testing for various designs. Each fixation feature was inserted and extracted from bone, with ratios calculated for each tested fixation feature indicative of the force of insertion versus the force of extraction. As such, high ratios would indicate any of a number of advantageous features for a given fixation feature including, for example, ease of fixation feature insertion into tissue and resistance to extraction, which would be indicative of fixation feature stability in the tissue (e.g., bone).

The three highlighted results are examples described by the concepts illustrated in FIGS. 2 to 6 and described in detail above. The result 710 illustrates the performance of a peg 104 (see FIGS. 2-3), and the result 712 illustrates the performance of the fixation feature 410 (see FIGS. 4-5), while the result 714 illustrates the performance of the fixation feature 610 (see FIG. 6). The three highlighted concepts performed as well as other pegs tested, which included devices similar to those with clinical usage. The results reinforce the advantageous nature of the various embodiments herein, which provide additional stability (e.g., as illustrated by the extraction/insertion force ratios of the embodiments disclosed herein).

Manufacturing Processes

The porous three-dimensional metallic structures disclosed above can be made using a variety of different metal component manufacturing techniques, including but not limited to: Casting Processes (casting processes involve pouring molten metal into a mold cavity where, once solid, the metal takes on the shape of the cavity. Examples include, expendable mold casting, permanent mold casting, and powder compaction metallurgy), Deformation Processes (deformation processes include metal forming and sheet metalworking processes which involve the use of a tool that applies mechanical stresses to metal which exceed the yield stress of the metal), Material Removal Processes (these processes remove extra material from the workpiece in order to achieve the desired shape. Examples of material removal processes include, tool machining and abrasive machining), and Additive Manufacturing Processes (these processes involve the use of digital 3D design data to build up a metal component up in layers by depositing successive layers of material). Additive Manufacturing Processes can include, only by way of example, powder bed fusion printing (e.g., melting and sintering), cold spray 3D printing, wire feed 3D printing, fused deposition 3D printing, extrusion 3D printing, liquid metal 3D printing, stereolithography 3D printing, binder jetting 3D printing, material jetting 3D printing, and so on. It should be appreciated, however, that additive manufacturing processes offer some unique advantages over the other metal component manufacturing techniques with respect to the manufacture of porous three-dimensional metallic structures (disclosed above) due to the complexities of the geometries and structural elements of the unit cells which comprise those types of structures.

Figure 8:
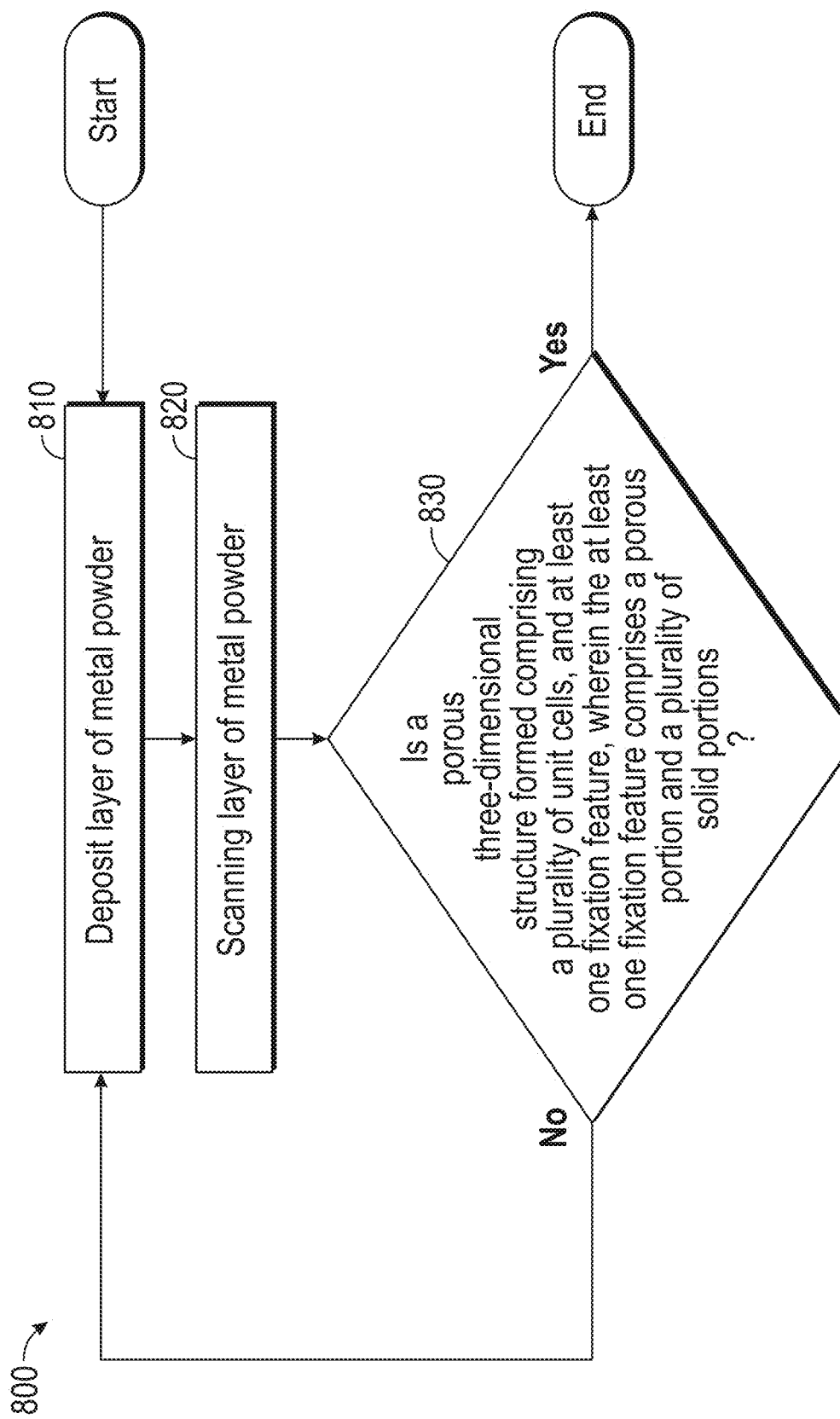
FIG. 8 depicts a flow chart of a method for manufacturing a porous three-dimensional structure, in accordance with various embodiments.

In accordance with various embodiments, a method for producing an orthopaedic implant is provided, for example, by method 800 illustrated in FIG. 8. The method can comprise depositing and scanning successive layers of metal powders with a beam to form a porous three-dimensional structure. The porous three-dimensional structure can comprise a plurality of unit cells and the depositing and scanning can form at least one fixation feature that extends beyond a surface boundary of the porous three-dimensional structure. The at least one fixation feature can be anchored to a first side of the porous three-dimensional structure and comprises a porous portion having an interior, at least one solid portion, and at least one slot at least partially located on the interior of the porous portion. The beam (or scanning beam) can be an electron beam. The beam (or scanning beam) can be a laser beam.

As provided in FIG. 8, step 810 includes depositing a layer of metal powder. Step 820 includes scanning a layer of metal powder. As provided in step 830, the steps 810 and 820 are repeated until a porous three-dimensional structure is formed comprising a plurality of unit cells, and at least one fixation feature is formed that extends beyond a surface boundary of the porous-three-dimensional structure, wherein the at least one fixation feature is anchored to a first side of the porous three-dimensional structure and comprises a porous portion and a plurality of solid portions positioned on an outside surface of the porous portion.

Regarding the various methods described herein, the metal powders can be sintered to form the porous three-dimensional structure. Alternatively, the metal powders can be melted to form the porous three-dimensional structure. The successive layers of metal powders can be deposited onto a solid base (see above for discussion regarding base).

In various embodiments, the types of metal powders that can be used include, but are not limited to, titanium, titanium alloys, stainless steel, cobalt chrome alloys, tantalum or niobium powders. In various embodiments, a second side of the porous three-dimensional structure can be anchored to the base.

In accordance with various embodiments, a method for producing an orthopaedic implant is provided. The method can comprise depositing and scanning successive layers of metal powders to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, providing a base, and anchoring a second side of the porous three-dimensional structure to the base.

In accordance with various embodiments, a method for producing a porous three-dimensional structure is provided. The method can comprise depositing and scanning successive layers of metal powders with a beam to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, providing a base, and anchoring a second side of the porous three-dimensional structure to the base. The beam can be an electron beam. The beam can be a laser beam. In various embodiments, the metal powders are sintered to form the porous three-dimensional structure. In various embodiments, the metal powders are melted to form the porous three-dimensional structure. In various embodiments, the successive layers of metal powders are deposited onto a solid base.

In accordance with various embodiments, a method for producing a porous three-dimensional structure is provided. The method can comprise applying a stream of metal particles at a predetermined velocity onto a base to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. The predetermined velocity can be a critical velocity required for the metal particles to bond upon impacting the base. The critical velocity can be greater than 340 m/s. The method can further include applying a laser at a predetermined power setting onto an area of the base where the stream of metal particles is impacting. In various embodiments, the types of metal particles that can be used include, but are not limited to, titanium, titanium alloys, stainless steel, cobalt chrome alloys, tantalum or niobium particles.

In accordance with various embodiments, a method for producing a porous three-dimensional structure is provided. The method can comprise introducing a continuous feed of metal wire onto a base surface and applying a beam at a predetermined power setting to an area where the metal wire contacts the base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. The beam can be an electron beam. The beam can be a laser beam. In various embodiments, the types of metal wire that can be used include, but are not limited to, titanium, titanium alloys, stainless steel, cobalt chrome alloys, tantalum or niobium wire.

In accordance with various embodiments, a method for producing a porous three-dimensional structure is provided. The method can comprise introducing a continuous feed of a polymer material embedded with a metal element onto a base surface and applying heat to an area where the polymer material contacts the base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. In various embodiments, the continuous feed of polymer material can be supplied through a heated nozzle thus eliminating the need for applying heat to the area where the polymer material contacts the base surface to form the porous three-dimensional structures. In various embodiments, the types of metal elements that can be used to embed the polymer material can include, but are not limited to, titanium, titanium alloys, stainless steel, cobalt chrome alloys, tantalum and niobium.

The method can further include scanning the porous three-dimensional structure with a beam to burn off the polymer material. The beam (or scanning beam) can be an electron beam. The beam (or scanning beam) can be a laser beam.

In accordance with various embodiments, a method for producing a porous three-dimensional structure is provided. The method can comprise introducing a metal slurry through a nozzle onto a base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. In various embodiments, the nozzle is heated at a temperature required to bond the metallic elements of the metal slurry to the base surface. In various embodiments, the metal slurry is an aqueous suspension containing metal particles along with one or more additive (liquid or solid) to improve the performance of the manufacturing process or the porous three-dimensional structure. In various embodiments, the metal slurry is an organic solvent suspension containing metal particles along with one or more additive (liquid or solid) to improve the performance of the manufacturing process or the porous three-dimensional structure. In various embodiments, the types of metal particles that can be utilized in the metal slurry include, but are not limited to, titanium, titanium alloys, stainless steel, cobalt chrome alloys, tantalum or niobium particles.

In accordance with various embodiments, a method for producing a porous three-dimensional structure is provided. The method can comprise introducing successive layers of molten metal onto a base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. The molten metal can be introduced as a continuous stream onto the base surface. The molten metal can be introduced as a stream of discrete molten metal droplets onto the base surface. In various embodiments, the types of molten metals that can be used include, but are not limited to, titanium, titanium alloys, stainless steel, cobalt chrome alloys, tantalum or niobium.

In accordance with various embodiments, a method for producing a porous three-dimensional structure is provided. The method can comprise applying and photoactivating successive layers of photosensitive polymer embedded with metal elements onto a base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. In various embodiments, the types of metal elements that can be used to embed the polymer material can include, but are not limited to, titanium, titanium alloys, stainless steel, cobalt chrome alloys, tantalum or niobium.

In accordance with various embodiments, a method for producing a porous three-dimensional structure is provided. The method can comprise depositing and binding successive layers of metal powders with a binder material to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, a base and anchoring a second side of the porous three-dimensional structure to the base. In various embodiments, the types of metal powders that can be used include, but are not limited to, titanium, titanium alloys, stainless steel, cobalt chrome alloys, tantalum or niobium powders.

The method can further include sintering or melting the bound metal powder with a beam. The beam can be an electron beam. The beam can be a laser beam. The method can further include sintering or melting the bound metal powder with a heating element, where the beam is an electron beam, or the beam is a laser beam.

In accordance with various embodiments, a method for producing a porous three-dimensional structure is provided. The method can comprise depositing droplets of a metal material onto a base surface, and applying heat to an area where the metal material contacts the base surface to form a porous three-dimensional structure comprising a plurality of unit cells and to form at least one fixation feature that extends beyond a surface boundary of the porous-three-dimensional structure. The at least one fixation feature can be anchored to a first side of the porous three-dimensional structure and comprises a porous portion and a plurality of solid portions positioned on an outside surface of the porous portion. The method can further comprise, in various embodiments, anchoring a second side of the porous three-dimensional structure to the base. The heat can be applied with a beam, wherein the beam is an electron beam. The heat can be applied with a beam, wherein the beam is a laser beam. The metal material can be a metal slurry embedded with metallic elements. The metal material can be a metal powder. In various embodiments, the types of metal materials that can be used include, but are not limited to, titanium, titanium alloys, stainless steel, cobalt chrome alloys, tantalum or niobium.

Although specific embodiments and applications of the same have been described in this specification, these embodiments and applications are exemplary only, and many variations are possible.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

Although specific embodiments and applications of the same have been described in this specification, these embodiments and applications are exemplary only, and many variations are possible.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. An orthopaedic prosthetic component, comprising:
   a base; and
   a fixation peg extending away from the base to a distal tip, the fixation peg including a porous three-dimensional structure configured to permit bone in-growth, the porous three-dimensional structure having an outer surface boundary,
   wherein the fixation peg includes a plurality of plates attached to the porous three-dimensional structure at the outer surface boundary, each plate including a tapered body having an outer wall that faces away from the porous three-dimensional structure and is devoid of any openings, and
   wherein the tapered body of each plate extends longitudinally along the porous three-dimensional structure, the tapered body of each plate extends from a proximal end to a distal end, and the tapered body of each plate has a first width at the proximal end and a second width greater than the first width between the proximal end and the distal end.

2. The orthopaedic prosthetic component of claim 1, wherein the outer wall of each plate includes a concave surface that defines a tapered channel.

3. The orthopaedic prosthetic component of claim 1, wherein the plurality of plates are arranged circumferentially on the porous three-dimensional structure.

4. The orthopaedic prosthetic component of claim 3, wherein adjacent plates of the plurality of plates are spaced apart circumferentially from each other on the porous three-dimensional structure.

5. The orthopaedic prosthetic component of claim 1, wherein the plurality of plates are positioned between the distal tip of the fixation peg and the base.

6. The orthopaedic prosthetic component of claim 1, wherein the base includes a tibial platform configured to receive a tibial insert.

7. The orthopaedic prosthetic component of claim 6, further comprising an elongated stem that extends from the tibial platform to a distal tip, the elongated stem being configured to be implanted in a surgically-prepared proximal end of a patient's tibia.

8. The orthopaedic prosthetic component of claim 7, further comprising a porous three-dimensional layer attached to a distal surface of the tibial platform,
   wherein the elongated stem extends outwardly from the three-dimensional layer, and the fixation peg extends outwardly from the porous three-dimensional layer.

9. The orthopaedic prosthetic component of claim 1, wherein:
   the tapered body of each plate extends from a proximal end to a distal end, and
   the tapered body of each plate has a first thickness at the distal end and a second thickness greater than the first thickness between the proximal end and the distal end.

10. The orthopaedic prosthetic component of claim 9, wherein each plate extends circumferentially around the porous three-dimensional structure.

11. The orthopaedic prosthetic component of claim 10, wherein adjacent plates of the plurality of plates are spaced apart from each other on the porous three-dimensional structure in a proximal-distal direction.

12. The orthopaedic prosthetic component of claim 10, wherein the distal tip of the fixation peg includes a longitudinal slot.

13. An orthopaedic prosthetic component, comprising:
a tibial platform configured to receive a tibial insert,
a porous three-dimensional structure coupled to the tibial platform, the porous three-dimensional structure being configured to permit bone in-growth, and
an elongated stem extending away from the tibial platform to a distal tip,
wherein the porous three-dimensional structure includes a layer coupled to the tibial platform and a plurality of fixation pegs extending from the layer, each fixation peg including a portion of the porous three-dimensional structure that has an outer surface boundary,
wherein a plurality of plates are attached at the outer surface boundary of each fixation peg, each plate including a tapered body that 1) extends longitudinally along the porous three-dimensional structure, and 2) has an outer wall that includes a concave surface that defines a tapered channel, wherein the outer wall is devoid of any openings, and
wherein the tapered body of each plate extends longitudinally along the porous three-dimensional structure.

14. The orthopaedic prosthetic component of claim 13, wherein adjacent plates of the plurality of plates are spaced apart circumferentially from each other on each peg.

15. The orthopaedic prosthetic component of claim 13, wherein adjacent plates of the plurality of plates are spaced apart from each other on the porous three-dimensional structure in a proximal-distal direction.

* * * * *